United States Patent [19]

Aday et al.

[11] Patent Number: 4,555,016
[45] Date of Patent: Nov. 26, 1985

[54] THREE-PANEL NEEDLED SUTURE HOLDER

[75] Inventors: Jorge L. Aday, Lambertville; Robert J. Cerwin, Pittstown, both of N.J.

[73] Assignee: Ethicon, Inc., Somerville, N.J.

[21] Appl. No.: 744,856

[22] Filed: Jun. 14, 1985

[51] Int. Cl.⁴ ............................................. A61L 17/02
[52] U.S. Cl. .................................... 206/63.3; 206/380
[58] Field of Search ...................... 206/63.3, 227, 380, 206/381, 382

[56] References Cited

U.S. PATENT DOCUMENTS

| | | | |
|---|---|---|---|
| 4,063,638 | 12/1977 | Marwood | 206/63.3 |
| 4,249,656 | 2/1981 | Cerwin et al. | 206/63.3 |
| 4,412,613 | 11/1983 | Kubas | 206/63.3 |
| 4,483,437 | 11/1984 | Cerwin et al. | 206/63.3 |

Primary Examiner—Joseph Man-Fu Moy
Attorney, Agent, or Firm—Robert L. Minier

[57] ABSTRACT

A three-panel needled suture retainer with a separate compartment for the needle and a separate compartment for the suture. The retainer includes die cut and foldable portions to readily expose the needle to the user.

7 Claims, 9 Drawing Figures

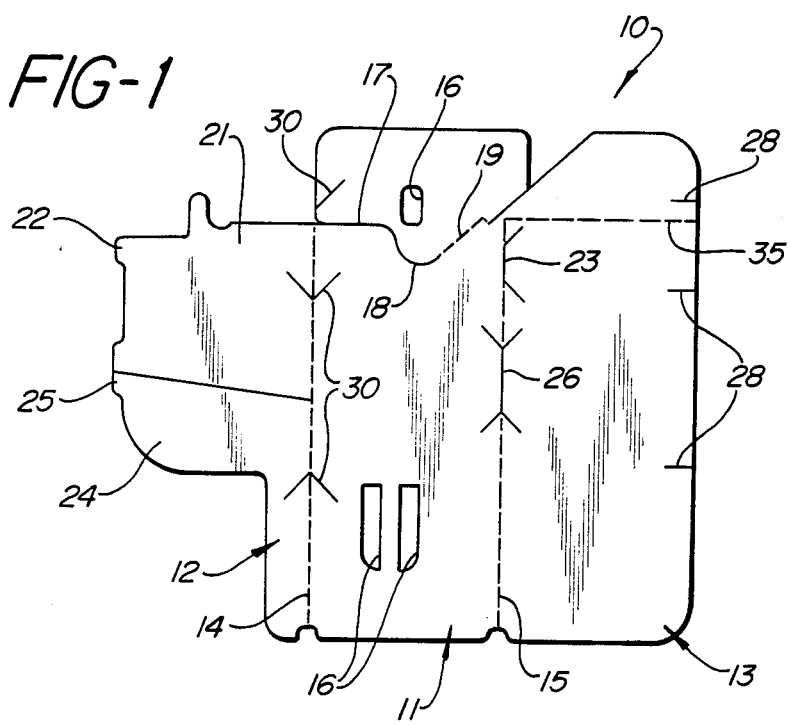
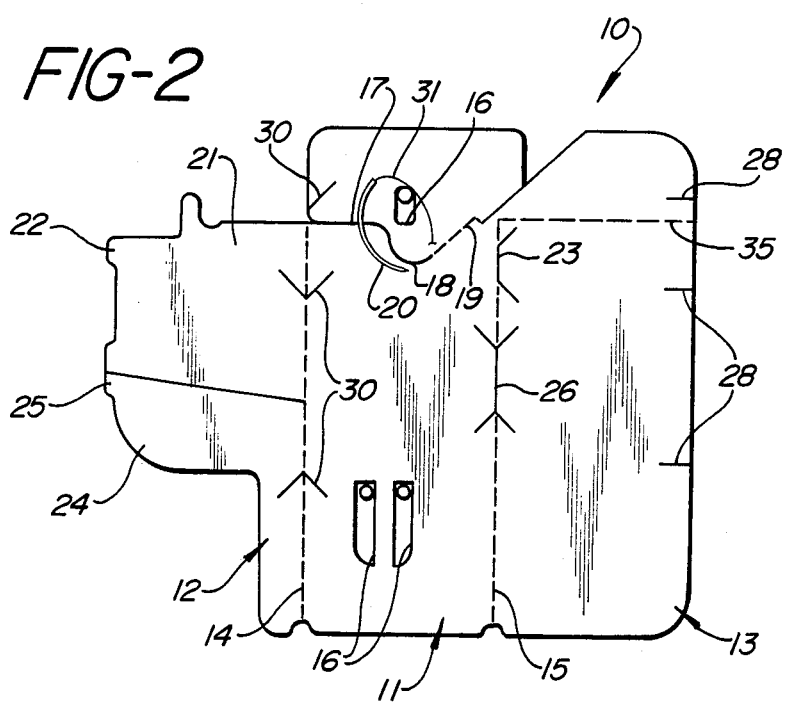

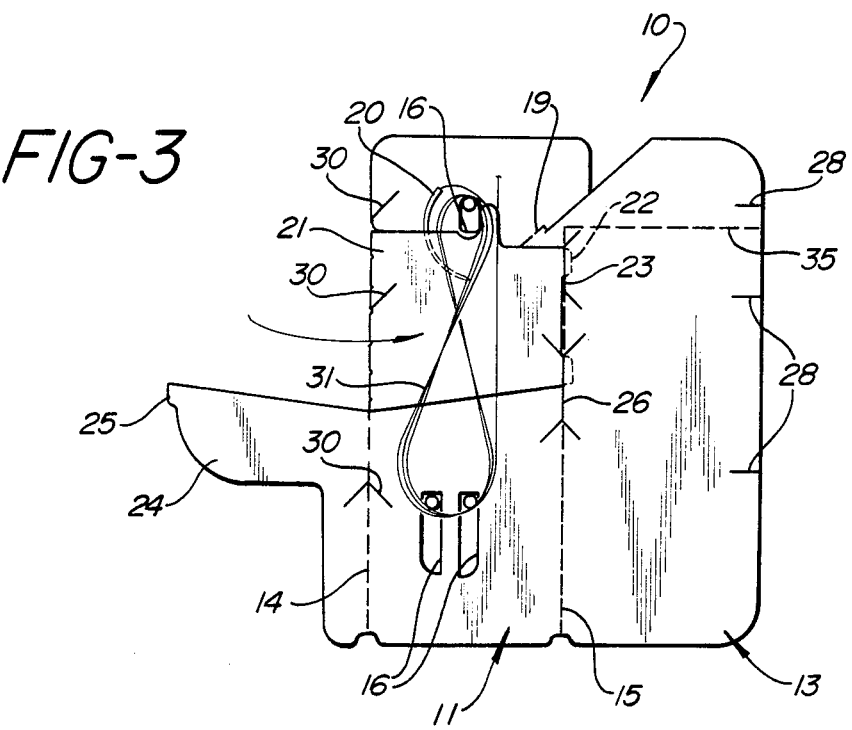
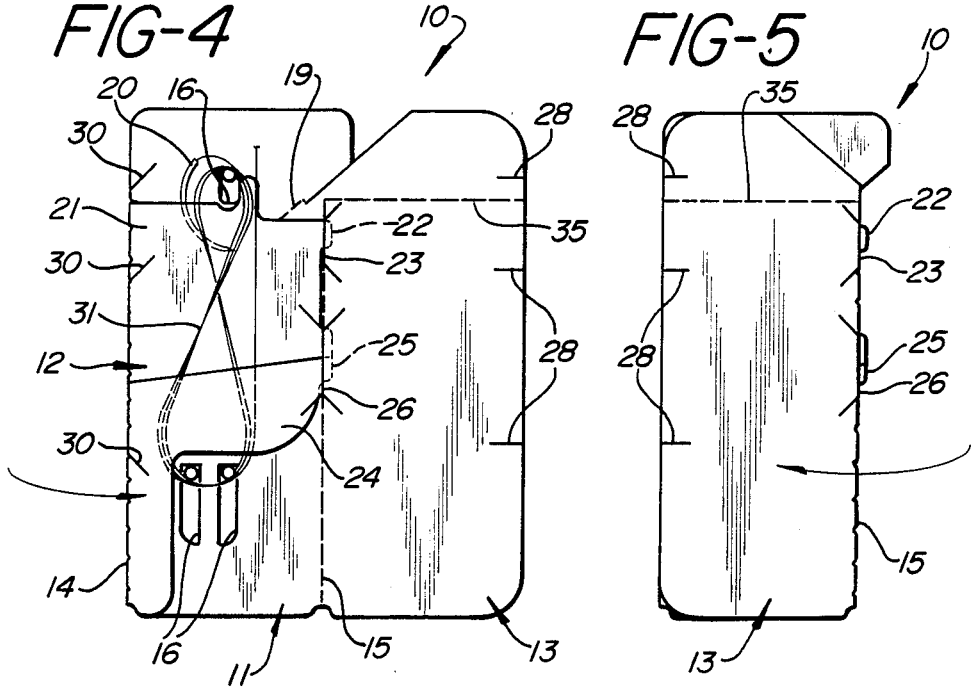

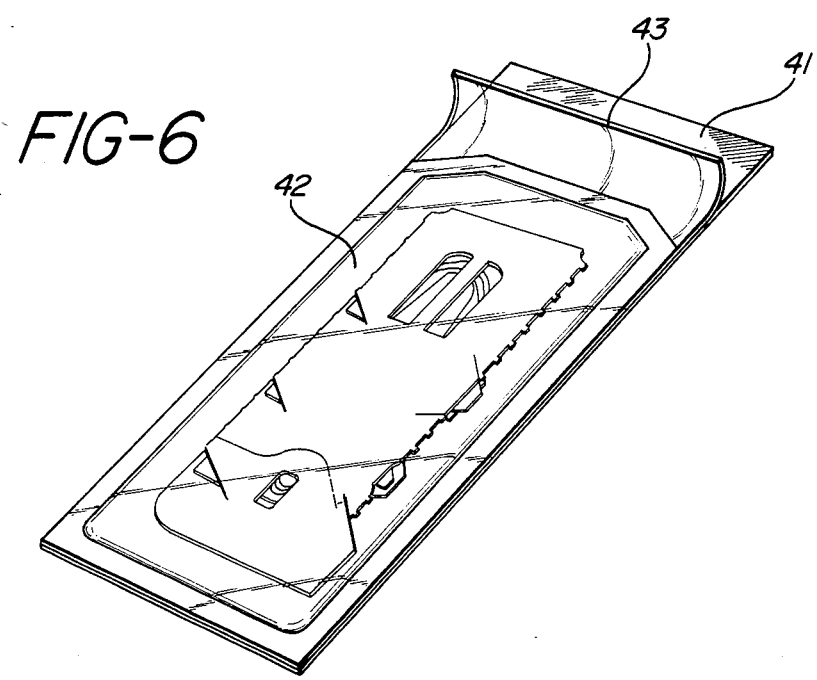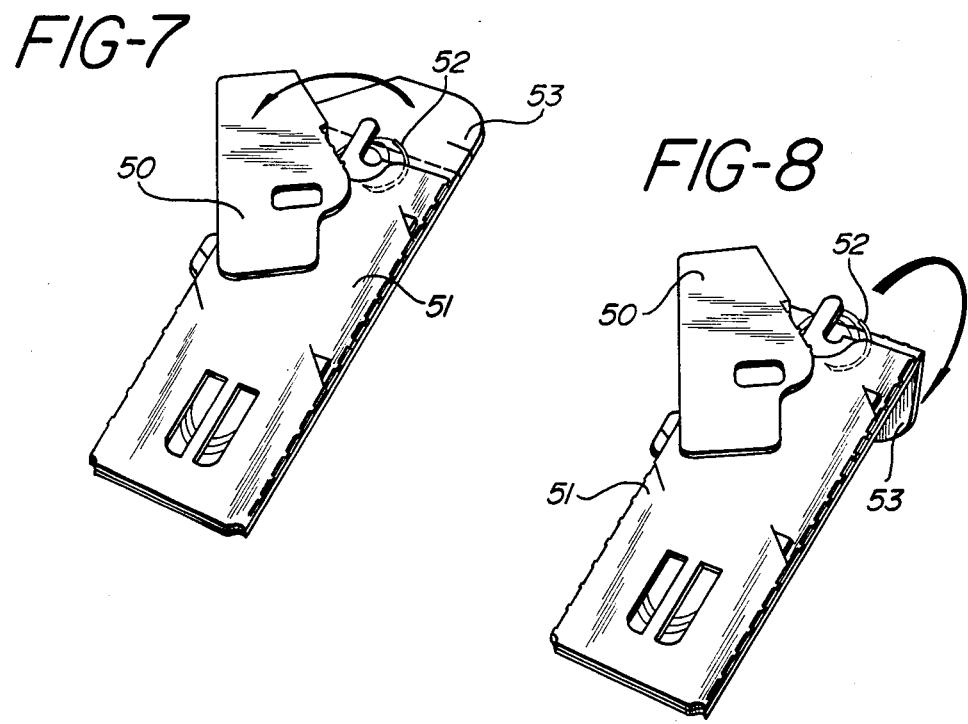

THREE-PANEL NEEDLED SUTURE HOLDER

DESCRIPTION OF THE INVENTION

The present invention relates to holders for needled surgical sutures and more particularly to a multipaneled folded retainer for a suture coil having a needle attached thereto.

Packages for surgical sutures are constructed according to the nature of the suture and its intended use. In general, the ideal package holds and protects the suture and needle during handling and storage, yet allows the suture and needle to be readily removed with a minimum of handling and difficulty.

In a needled suture package it is preferred that the needle be maintained in a separate compartment to prevent the needle from cutting or damaging the suture and also prevent any dulling or damage to the sharp cutting edges of the needle. It is also preferred that the retainer for the needled suture be so constructed that when placed in a package and sterilized and the package then presented in a sterile condition to the operating theater, it is a simple operation to open the package and present the needle to the user so it can be easily and readily gripped by a suitable instrument while all the time being maintained in a sterile condition. There are a number of suture packages which accomplish these desirable results, such as those described in U.S. Pat. Nos. 3,444,944, 3,939,969, 4,014,434 4,253,563 and 4,249,656. There are, of course, many more patents which describe various types of needled suture retainers.

In producing these suture packages, generally the retainer is placed on a plurality of pins which fit through apertures in the retainer. The retainer is slipped over the pins, the needle held in some manner and the suture wound about the pins in a figure-8 or like configuration. The retainer is folded in various manners to secure the needle and the wound suture within the retainer. The retainer is placed inside a foil or other package sterilized and appropriately over wrapped to maintain sterilization.

Though many of these suture retainers have gained wide acceptance in the marketplace and in the hospital and surgical area, they all suffer from some problem relating to the manufacture and the production of the wound suture in the retainer. This winding operation is usually a hand operation or, in some instances, semiautomatic and it is becoming apparent that the suture windings, because of their configuration, place undue stresses on the wrist and finger joints of the individual winding and placing the needle suture in the retainer.

Recently, an improved suture retainer, as described in U.S. Pat. No. 4,412,614 has been developed, which eliminates many of the manufacturing problems and greatly reduces any strain placed on the wrist or finger joints of the winder. While such a retainer has gained wide acceptance to improve the manufacture of the suture retainer, neither the retainer described in U.S. Pat. No. 4,412,614 or any other prior art produces a retainer that not only allows for automatic winding, but presents the needle to either a right handed or left handed user in a very simple and convenient manner. Our improved retainer also allows for the user to open the container and present the needle utilizing only one hand. Our new retainer also allows the needle to be presented in a manner that the instrument used to grip the needle may be placed at any desired and adjustable depth on the needle for easy and reliable grasping of the needle.

SUMMARY OF THE PRESENT INVENTION

In its broadest aspects this invention relates to a three-panel folded retainer for holding a needled surgical suture. One of the panels is sectioned to separately lock or hold the needle in place and away from the remainder of the suture and with the other section of this panel holding the suture in place without interfering with the winding of the suture. The three panels are interlocked to retain the needled suture in its desired form so that it can be handled, packaged, sterilized, transported, opened and presented for use in a sterile, easy, usable form when desired.

One of the panels is slit and has a scored line to allow for single handed folding of that portion of the panel. Another panel also has a fold line which can be folded back with one hand to totally expose the needle to the needle holding instrument.

The improved retainer for a needled surgical suture of the present invention comprises a center panel and a pair of side panels. The center panel is substantially rectangular in shape and the side panels are attached to each longitudinal edge of the center panel. The center panel has a plurality of apertures located therein. At least one aperture is located adjacent one of the shorter sides of the center panel and at least one aperture is located adjacent the opposite shorter side of the center panel. In the preferred embodiment, there are a plurality of apertures located adjacent each shorter side. The apertures are adapted to accept pins which protrude through the apertures when the retainer is placed over the pins. The suture itself is wound about these pins in the desired figure-8 or similar configuration.

One of the side panels is configured so that when it is folded on the center panel it is substantially coextensive with the center panel in the central portion of the center panel but does not cover any of the apertures located in the center panel. This side panel is sectioned transversely into two sections. This sectioning allows the needle to be placed on the center panel adjacent one group of apertures and to fold the first section of the side panel onto the center panel holding the needle in place. This section of the panel is configured so as not to interfere with the winding pins. The suture is then wound about the pins through the apertures down around the opposite pins protruding through the other apertures. This immediately holds the sectioned side piece down on the needle and locks the needle in place so that the operator is no longer required to hold the needle. After the suture is completely wound the second section of the side panel is folded over holding the wound suture in place. The second side panel is substantially coextensive with the center panel and foldable about the longitudinal edge thereof. The center panel, at a position just below, or at approximately the same position as the upper edge of the sectioned side panel, has a slit or a plurality of slits extending from the longitudinal edge or edges of that center panel towards the center of the center panel so that approximately one half of the width of the center panel has been slit. From the end of the slit to the opposite longitudinal edge, or connecting slits if plural slits are used, is a scored line. In a preferred embodiment of this invention, a single slit extending from one longitudinal edge is used with the slit ending in a semicircular slit from which the scored line then extends. By totally slitting at least half the center panel and scoring the remainder of the width of the panel, it is a simple mechanism for the user to take an upper corner of the center panel immediately above a slit portion and, with slight pressure, fold the slit and scored portion of the center panel back away exposing the needle.

The second side panel has a foldable line at a position close to its upper end and just below or at the top portion of the sectioned side panel holding the needle. As can be appreciated, this portion may also be folded back after the portion of the center panel is folded back totally exposing a portion of the needle in a manner that allows a needle gripping instrument to be adjustably positioned on the needle and the needle grasped by the instrument at any desired depth in the jaws of the instrument. As can be appreciated, the panel may be utilized in a very simple manner either by a right or left handed user merely by turning over the suture retainer.

BRIEF DESCRIPTION OF THE DRAWINGS

The invention will be more fully described when taken in conjunction with the accompanying drawings wherein:

FIG. 1 is a plan view of the unfolded suture retainer of the present invention;

FIG. 2 is a plan view of the unfolded suture retainer of FIG. 1 with the needle being placed in the center panel and the suture starting to be wound about a single pin;

FIG. 3 is a plan view of the suture retainer of FIG. 1 with the first section of one of the side panels folded over on the needle and the suture being wound about the pins;

FIG. 4 is a plan view of the suture retainer of FIG. 3 with one side panel folded over the needle and the suture;

FIG. 5 is a plan view of the folded suture retainer of FIG. 4;

FIG. 6 is a perspective view of the fully folded suture retainer of FIG. 5 contained within a sealed outer envelope;

FIG. 7 is a perspective view of a folded retainer of the present invention having a portion of one panel folded away to partially expose the needle;

FIG. 8 is a perspective view of the folded suture retainer of the present invention having portions of two panels folded away to fully expose the needle in the retainer.

DETAILED DESCRIPTION OF THE INVENTION

Figure 9:
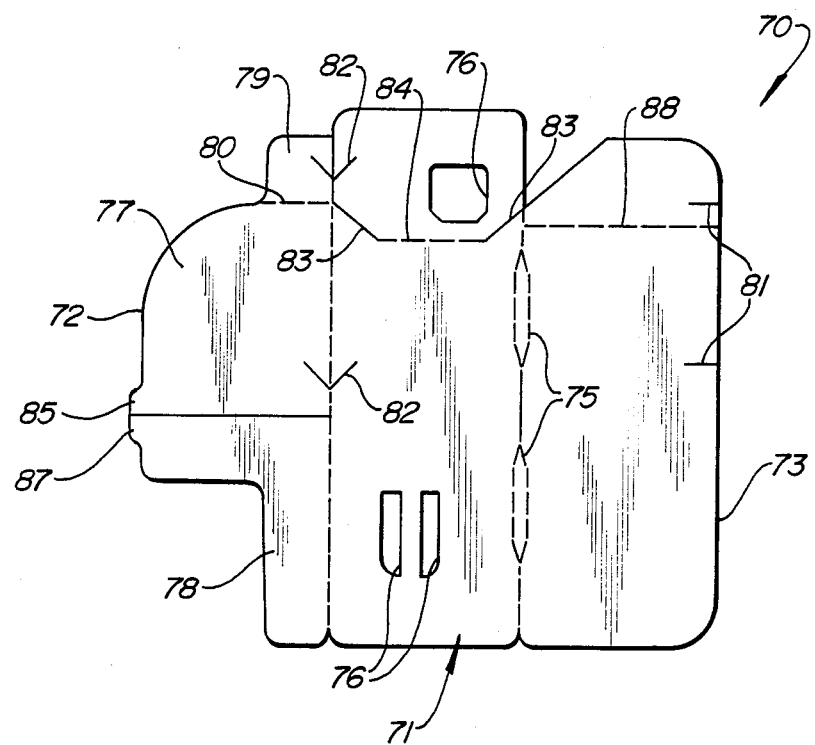
FIG. 9 is a plan view on another embodiment of an unfolded suture retainer of the present invention.

FIGS. 1-5 illustrate the various stages in folding the suture retainer of the present invention.

In FIG. 1, there is illustrated an open suture retainer 10 comprising a center panel 11 and a pair of side panels 12 and 13.

The center panel is generally rectangular in shape and the side panels are connected to the longitudinal edges along the longer sides of the center panel. The side panels are connected at foldable lines 14 and 15 to the longitudinal edges of the center panel. The center panel includes a plurality of apertures 16. In this embodiment there is one aperture at the upper shorter side of the center panel for accepting the pin on which a suture may be wound and there are a pair of apertures adjacent the lower shorter side of the center panel for accepting a pair of pins on which the suture is wound.

One of the side panels is separated in two sections, as will be explained hereinafter. The retainer also includes a plurality of slits at the edges of the side panels to provide a locking means, this again will be described hereinafter. The center panel includes a die cut area just below the single aperture. The die cut area comprises a slit 17 extending from one longitudinal edge of the center panel, towards the center of the panel with a semicircular slit 18 at the center of the panel. Extending from the slit to the other edge of the center panel is a circular scored diagonal line 19 so the top portion of the center panel may be easily folded away or back on the center panel. This provides ready exposure of the needle 20 when it is desired that the suture be used, as will be more fully described in conjunction with FIG. 7.

In placing the needle suture in the retainer, the needle is first placed, as shown in FIG. 2, in the position it is desired to be in in the final package. Once the needle has been placed and the suture started to be wound about the single pin protruding through the aperture, the upper section 21 of the sectioned side panel 12 is folded over the needle, as shown in FIG. 3. This sectioned area 21 holds the needle in the desired position and separates the needle, from the remainder of the suture so that during further processing, storage, sterilization and transportation nothing will damage the needle or suture. This section 21 of the side panel has a tab 22 which is locked into the slit 23 in the fold line between the center panel and the opposite side panel. The suture 30 is then wound from the single pin over the folded section of the side panel and places pressure on the section to hold the needle in place. Any outside pressure being placed to hold the needle may now be removed and the suture continued to be wound. The suture is wound from the single pin and around the double pins at the lower end of the center panel. Preferably this suture is wound in a figure-8 configuration, as shown, other configurations may also be used.

When the suture has been completely wound about the pins the second section 24 of the sectioned side panel 12 is folded over the bottom potion of the sutures, as is more fully shown in FIG. 4, holding the sutures in place. This section also has a tab 25 at its free edge which fits into a slit 26 in the fold line between the center panel and the opposite side panel. This folding places the needle in one pocket within the three-panel folder and the suture in another separate pocket of the three-panel folder. Once the retainer is completely folded it is locked, as more clearly shown in FIG. 5, by engaging slits 28 in the unconnected longitudinal edge of the side panel 13 with the complementary locking slits 30 in the folded edge between the center panel and the opposite side panel.

Though a combination of slits is shown, it is clear that other locking means may be used, such as tabs at one edge which fit into slits at the opposite edge and the like.

The suture folder of the present invention is preferably constructed of heavy-weight relatively stiff paper or paper board, such as 5 to 12 point solid bleached sulfate board. This paper board is readily foldable and yet sufficiently strong and stiff to support the needled suture and provide a relatively rigid package. Similar materials, including plastics, foils and laminates of combinations with each other or with paper can also be used with good results. The folder can be readily cut from such materials by a single die which also forms the desired fold lines in accordance with the present invention.

In the opposite side panel 13, which is substantially coextensive with the center panel, there is a fold line 35 at the upper edge of that side panel at the same edge with the die cut portion of the center panel. The operation of this folded edge will be more fully described in conjunction with FIG. 8.

As may be seen from the prior description, once the needle is placed and the first section of the side panel folded over on the needle and the suture brought down on top of this sectioned piece to the winding pins, the operator may remove any pressure required to hold the needle in place, and hence relieve any stress being placed on the operators hand in holding the needle while winding the suture. The folder works with various size needles and once the operator has placed the needle, it is a simple matter for a mechanical winder to wind the suture in a desired configuration.

Referring to FIG. 6, the fully folded retainer and suture of FIG. 5 is subsequently sterilized and sealed within a sterile outer envelope, as illustrated in FIG. 6. The envelope is a conventional suture package envelope formed by heat sealing the periphery of two panels 40 and 41, one of coated paper and the other of a thermoplastic film, which are coated on a surface with a heat sealable polymeric composition 42. One shorter edge of this outer envelope has a portion 42 not sealed so the two layers may be readily pealed apart to expose the full folded retainer.

As seen in FIG. 7, the folded retainer has been removed from the sealed envelope. The user may now, utilizing his thumb, readily fold back the die cut portion 50 of the center panel 51 to expose the needle 52. This may be easily done by holding the retainer in one hand, either the left of right hand, and with the thumb putting sufficient pressure on the die cut portion to fold it diagonally away from the remainder of the retainer and expose the needle.

As seen in FIG. 8, it is now a simple matter for the user to take another finger and fold back the upper portion 53 of the side panel coextensive with the center panel. This fully exposes the needle and allows the user to grasp the needle to any depth utilizing a suitable needle grasping instrument.

As can be appreciated, this greatly simplifies presenting the needle to the user for use. The retainer may be utilized by either a right or left handed person and will fully expose the needle to allow the user to adjust the depth to which he desires to grip the needle.

In FIG. 9, there is illustrated another embodiment of an open suture retainer 70 of the present invention comprising a center panel 71 and a pair of side panels 72 and 73. The center panel is generally rectangular in shape and the side panels are connected to the longitudinal edges along the longer sides of the center panel. The side panels are connected at foldable lines 74 and 75 to the longitudinal edges of the center panel. The fold lines 75 double fold lines to form a gusset between the center panel and the side panel 73. The center panel includes a plurality of apertures 76. in this embodiment there is also one aperture at the upper shorter side of the center panel for accepting the pin on which a suture may be wound and there are a pair of apertures adjacent the lower shorter side of the center panel for accepting a pair of pins on which the suture is wound.

One of the side panels 72 is separated in two sections 77 and 78. The upper portion of 77 includes a foldable line 80 to allow section 79 to be folded back in the final folded retainer. The retainer also includes a plurality of slits 81 at the free edge of the side panel 73 and slit 82 at the folded line 74 which engage when the retainer is folded to provide a locking means. The center panel includes a die cut area just below the single aperture. The die cut area comprises a pair of slits 83 extending from the longitudinal edges of the center panel towards the center of the panel with the slits connected by a foldable line 84, so the top portion of the center panel may be easily folded away or back on the center panel. This provides ready exposure of the needle when it is desired that the suture be used.

The section 77 of the side panel has a tab 85 which is locked into the slit 86 in the fold line between the center panel and the opposite side panel. Section 78 also has a tab 87 at its free edge which fits into the slit 86 in the fold line between the center panel and the opposite side panel to lock the panels together. In the opposite side panel 73, which is substantially coextensive with the center panel, there is a fold line 88 at the upper edge of that side panel at the same edge with the die cut portion of the center panel.

As may be seen from the prior description, the needle is placed, the suture wound and the folder folded in the manner similar to that described in conjunction with FIGS. 2 through 5.

The needled sutures packaged in the retainers of the present invention may be multifilament or monofilament sutures and the multifilament sutures may be braided, twisted or coated. The needles may be of varying sizes, as desired.

The foregoing description has been drawn to a preferred embodiment of the present invention and many variations, which nevertheless employ the essential features thereof, will be apparent to those skilled in the art.

We claim:

1. An improved retainer for needled surgical sutures comprising:
   (a) a center panel;
   (b) a pair of side panels;
   (c) said center panel being substantially rectangular in shape;
   (d) a side panel foldably connected to each of the longitudinal edges of the center panel;
   (e) at least one upper aperture located adjacent one transverse edge of said center panel through which a pin may protrude on which the suture may be wound;
   (f) at least one lower aperture located adjacent the opposite transverse edge of said center panel through which a pin may protrude on which the suture may be wound;
   (g) one of said side panels being configured so that when it is folded upon the center panel it is substantially coextensive with the center panel in the central portion thereof but does not cover the apertures;
   (h) said side panel being sectioned transversely so that the needle of the needle surgical suture may be placed on the center panel adjacent the upper aperture and the first section of said side panel folded over on to the center panel to cover and enclose a portion of the needle without covering the entire needle or said upper aperture, whereby when the suture is wound about the pins protruding from the apertures the initial winding of the suture will hold the needle in place while the suture is being wound about the pins;

(i) the second section of said side panel being foldable over the center panel to contain the lower portion of the wound sutures;

(j) the other side panel being substantially coextensive with the center panel and foldable about the longitudinal edge thereof connecting said side panel to the center panel;

(k) said center panel including at least one slit extending from a longitudinal edge of said panel towards the center of said panel, said slit being positioned below but in close proximity to said upper aperture;

(l) a scored line extending from the end of said slit towards the opposite longitudinal edge of said center panel, whereby a portion of said center panel can be folded back to expose a needled surgical suture within the retainer;

(m) said other side panel having a fold line extending across the width of the panel, said fold line being spaced from a transverse edge of said panel so as to be adjacent said upper apertures when the panels are folded together, whereby when the portion of the center panel is folded back to expose the needled suture a portion of the side panel may also be folded back to fully expose the needled suture and allow for adjustable accessing of the needled suture in an appropriate needle holding instrument; and (n) said folder including locking means to maintain the folded panels in place and maintain the needled surgical suture in the desired configuration.

2. An improved retainer according to claim 1 wherein the center panel has two slits, one slit extends from one longitudinal edge of said panel towards the center of said panel and the second slit extends from the opposite longitudinal edge of said panel towards the center of said panel and the second line connects the two slits.

3. An improved retainer according to claim 1 wherein the center panel has one slit, said slit extends from a longitudinal edge of said panel approximately halfway across the width of said panel and the second line extends from the end of said slit in the center of the panel to the opposite longitudinal edge of the panel.

4. An improved retainer according to claim 4 wherein the slit in the center panel and the scored line in the center panel are connected by a circular slit portion.

5. An improved retainer according to claim 3 wherein the scored line extending from the end of the slit in the center panel to the opposite longitudinal edge of said center panel is a diagonal line.

6. A suture package comprising in combination a folded retainer of claim 1, 2 or 3 and a needled suture, the needle of said suture being positioned between the center panel and a first section of the sectioned side panel with the portion of the needle attached to the suture extending beyond the edge of said sectioned side panel.

7. A suture package of claim 6 enclosed in an outer envelope sealed around the periphery thereof.

* * * * *